US006599124B2

(12) United States Patent
Nakanishi

(10) Patent No.: US 6,599,124 B2
(45) Date of Patent: Jul. 29, 2003

(54) DENTAL HANDPIECE WITH ANGULAR CONTACT BALL BEARINGS

(75) Inventor: Takasuke Nakanishi, Kanuma (JP)

(73) Assignee: Nakanishi Inc., Tochigi-ken (JP)

( * ) Notice: Subject to any disclaimer, the term of this patent is extended or adjusted under 35 U.S.C. 154(b) by 0 days.

(21) Appl. No.: 10/073,249

(22) Filed: Feb. 13, 2002

(65) Prior Publication Data

US 2002/0110781 A1 Aug. 15, 2002

(30) Foreign Application Priority Data

Feb. 13, 2001 (JP) ....................................... 2001-035454

(51) Int. Cl.[7] .................................................. A61C 1/05
(52) U.S. Cl. ....................................................... 433/132
(58) Field of Search ................................ 433/132, 115, 433/82, 126, 127, 131

(56) References Cited

U.S. PATENT DOCUMENTS 5,252,065 A * 10/1993 Nakanishi .................. 433/115
5,252,067 A * 10/1993 Kakimoto ................... 433/126
5,676,542 A * 10/1997 Lingenhole et al. ........ 433/115
5,807,108 A * 9/1998 Schwenoha et al. ........ 415/904
5,911,579 A * 6/1999 Nakanishi ................... 433/132
6,099,308 A 8/2000 Nakanishi ................... 433/115

* cited by examiner

*Primary Examiner*—Kevin Shaven
*Assistant Examiner*—Melba Bumgarner
(74) *Attorney, Agent, or Firm*—Keil & Weinkauf

(57) ABSTRACT

A dental handpiece is disclosed, which includes a burr sleeve, upper and lower ball bearings for rotatably supporting the burr sleeve, a rotor fixed to the burr sleeve between the upper and lower ball bearings and rotated for rotatably driving the burr sleeve, and a dust controller. The dust controller includes a rotary protruding member fixed on the outer surface of the burr sleeve and rotating integrally with the burr sleeve, and a stationary protruding member attached to a stationary part of the handpiece and having a surface facing to the rotary protruding member to define a gap therebetween located outside of the lower ball bearing. The upper and lower ball bearings are angular contact ball bearings each having a bearing cage. The bearing cage has apertures that support bearing balls therein and are located in the middle of the bearing cage in the thrust direction.

6 Claims, 4 Drawing Sheets

DENTAL HANDPIECE WITH ANGULAR CONTACT BALL BEARINGS

FIELD OF THE INVENTION

The present invention relates to a dental handpiece, in particular a dental handpiece having angular contact ball bearings.

BACKGROUND OF THE INVENTION

Conventional dental handpieces having angular contact ball bearings have a general structure as shown in FIG. 3, in which head housing 11 accommodates burr sleeve 13, rotor 16, and ball bearings 34, 35. The burr sleeve 13 detachably holds a dental treatment tool 9 therein, and is rotatably supported by the upper and lower bearings 34, 35. The rotor 16 is fixed to the burr sleeve 13 between the upper and lower ball bearings 34, 35, and rotated by compressed air for rotatably driving the burr sleeve 13. The head housing 11 is capped with head cap 18, which is provided with spring 17 and push button 19, and screwed into the head housing 11.

The upper and lower bearings 34, 35 are of the angular contact type, wherein the groove on the outer rings 34*b*, 35*b*, i.e. the outer race, is tapered or angled. To each of the outer rings 34*b*, 35*b* is attached shield cover 37 using retaining ring 36 for preventing dust, such as debris, from intruding into the bearing. A plurality of balls 34*c*, 35*c* are supported at regular circumferential intervals by bearing cages 34*d*, 35*d*. The bearing cages 34*d*, 35*d* are in the form of a ring having a plurality of pockets 34*e*, 35*e* for supporting the balls 34*c*, 35*c* therein, as shown in FIGS. 4(*a*) and 4(*b*) in side and cross sectional views, respectively.

In the conventional dental handpieces as discussed above, the shield covers 37 interposed between the inner 34*a*, 35*a* and outer rings 34*b*, 35*b* restrict the spaces available for the bearing cages 34*d*, 35*d*. In order to be adapted to this restricted spaces, portions 34*d*′, 35*d*′(FIGS. 4(*a*) and 4(*b*)) of the cages 34*d*, 35*d* facing to the shield covers 37 have to be made smaller, resulting in difference in size between the portions above and below the pockets 34*e*, 35*e* of the bearing cages 34*d*, 35*d*.

Due to such asymmetry, when the burr sleeve 13 is rotated, the bearing cages 34*d*, 35*d* become unstable and contact the balls 34*c*, 35*c*, rattling up and down. This causes abrasion and wearing of the balls 34*c*, 35*c* and bearing cages 34*d*, 35*d* to damage these parts, and also causes undesirable shaking of the handpiece to generate uncomfortable noise.

The asymmetrical bearing cages 34*d*, 35*d* also add to the manufacturing cost of the dental handpiece. In automated assembly of the ball bearings 34, 35, the orientation of the retainers 34*d*, 35*d* has to be adjusted as predetermined by the vertically asymmetrical nature of the bearing cages 34*d*, 35*d*, which requires special systems and steps.

SUMMARY OF THE INVENTION

The present invention has been made to overcome these drawbacks of the conventional dental handpieces. It is therefore an object of the present invention to provide a dental handpiece wherein abrasion and wearing the balls and bearing cages in ball bearings are minimized.

It is another object of the present invention to provide a dental handpiece of which manufacturing cost is suppressed.

It is another object of the present invention to provide a dental handpiece having angular contact ball bearing wherein intrusion of duct into the bearings are effectively prevented.

According to the present invention, there is provided a dental handpiece comprising:

a burr sleeve for detachably holding a dental treatment tool therein;

upper and lower ball bearings for rotatably supporting said burr sleeve;

a rotor fixed to said burr sleeve between said upper and lower ball bearings and rotated by compressed air for rotatably driving said burr sleeve; and a dust controller including a rotary protruding member fixed on an outer surface of said burr sleeve and rotating integrally with said burr sleeve, and a stationary protruding member attached to a stationary part of said handpiece and having a surface facing to said rotary protruding member to define a gap therebetween, said gap being located outside of said lower ball bearing;

wherein said upper and lower ball bearings are angular contact ball bearings each having a bearing cage, said bearing cage having apertures for supporting balls of said ball bearings therein, said apertures being located substantially in the middle of said bearing cage in a thrust direction.

According to one aspect of the present invention, the conventional shield cover interposed between the inner and outer rings of a ball bearing of conventional dental handpieces is dispensed with, and instead a dust controller is placed outside of the ball bearing to expand the space between the inner and outer rings available for a bearing cage. This expanded space allows a vertically symmetrical bearing cage, i.e., a bearing cage having ball pockets substantially in the middle in the thrust direction, to be disposed between the inner and outer rings of the bearing. This vertically symmetrical bearing cage exhibits improved stability upon rotation of the burr sleeve, and thus minimizes shaking and noise of the handpiece. Further, use of the vertically symmetrical bearing cage eliminates special systems and steps for adjusting the vertical orientation of the bearing cage in automated assembly of the ball bearings, which reduces manufacturing cost of the handpiece.

According to another aspect of the present invention, a dental handpiece having an air turbine wherein a burr sleeve is rotated with compressed air, is provided with a dust controller including a rotary protruding member and a stationary protruding member. The rotary protruding member is fixed on and protrudes from the outer surface of the burr sleeve, and is rotated integrally therewith. The stationary protruding member is attached to and protrudes from a stationary part of the handpiece, and has a surface facing to the rotary protruding member to define a gap therebetween. The gap is located outside of the ball bearing.

The interior of the lower ball bearing communicates with the outside of the head housing via the dust controller. Rotation of the dust controller creates a high-pressure region between the rotation space of the rotor and the outside of the head housing. This high pressure region effectively blocks off air flow out of the head housing, and prevents suction of debris, saliva, blood, and the like through the lower end of the head housing upon stopping of the rotation of the rotor, which creates negative pressure in the head housing during rotation.

In the present invention, the stationary protruding member may be of any shape and configuration, as long as it does not narrow the space between the inner and outer rings of the ball bearing, and has a surface facing to the rotary protruding member to define a gap therebetween, which gap is located outside of the lower ball bearing. For example, the stationary protruding member may be generally in the form of an annular ring, of which radially outer end portion is fixed to the outer ring of the ball bearing, and of which radially inner end portion is extended radially inwardly beyond the inner ring of the ball bearing and defines a surface that faces to the rotary protruding member with a gap formed therebetween. The stationary protruding member may be attached to any stationary part of the handpiece, for example, to the outer ring of the ball bearing.

BRIEF DESCRIPTION OF THE DRAWINGS

The present invention will now be explained in detail with reference to the attached drawings showing illustrative examples of the invention, wherein:

FIG. 2(*b*) is a sectional view taken along lines IIb—IIb in FIG. 2(*a*);

FIG. 2(*c*) is a cross sectional view taken along lines IIc—IIc in FIG. 2(*a*);

FIG. 4(*b*) is a sectional view taken along lines IVb—IVb in FIG. 4(*a*).

PREFERRED EMBODIMENT OF THE INVENTION

Figure 1:
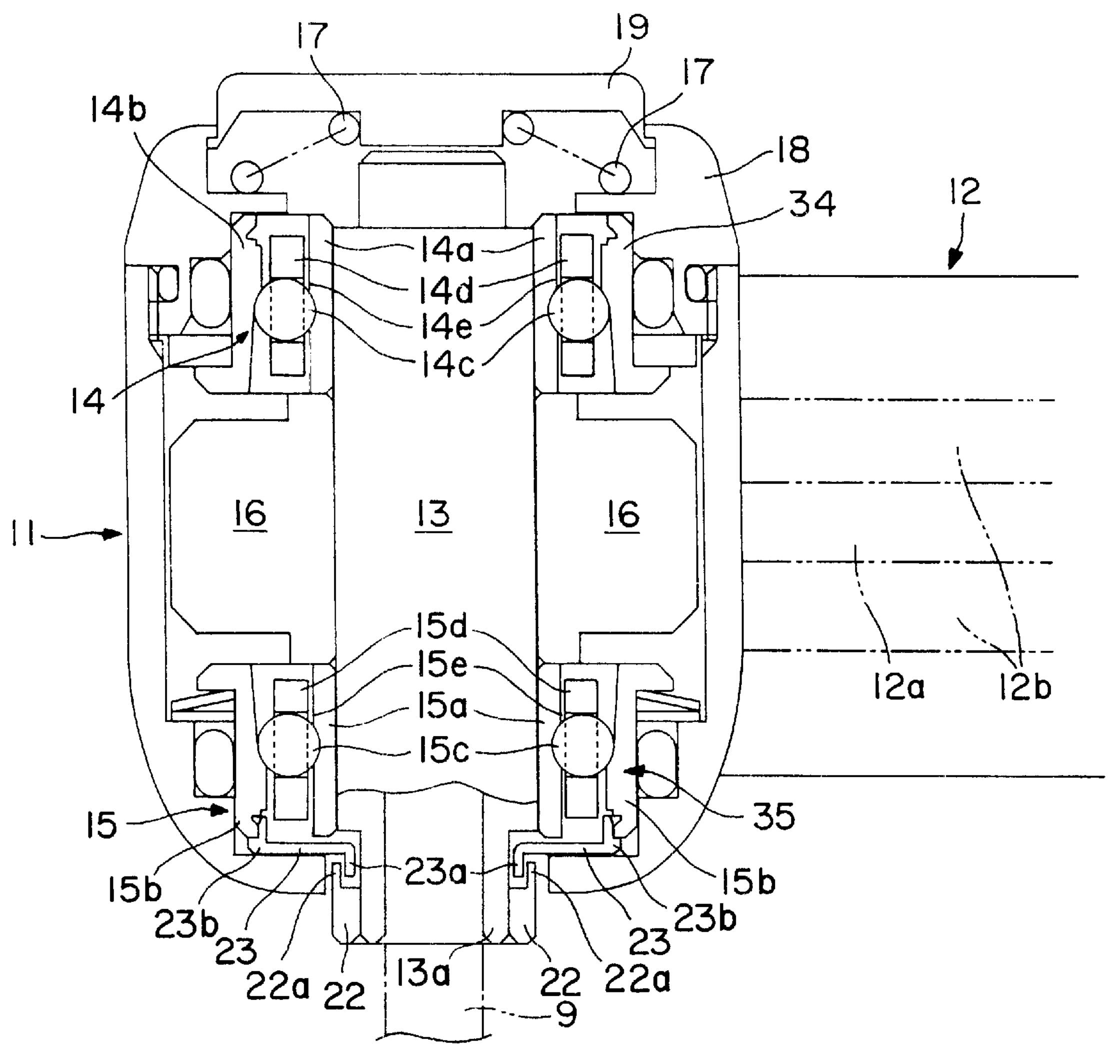
FIG. 1 is a schematic sectional view of a dental handpiece according to the present invention.

FIG. 1 illustrates a dental handpiece according to the present invention. The handpiece includes head housing 11, which accommodates burr sleeve 13 for detachably holding dental treatment tool 9 therein, upper and lower ball bearings 14, 15 for rotatably supporting the burr sleeve 13, and rotor 16 fixed to the burr sleeve between the upper and lower ball bearings and rotated by compressed air for rotatably driving the burr sleeve 13. A dust controller including rotary protruding member 22 and stationary protruding member 23 is provided near the lower end of the burr sleeve 13. Head cap 18 is screwed into the head housing 11, which cap 18 is provided with spring 17 and push button 19. The head housing 11 is connected to head housing jacket 12, which accommodates air supply line 12*a* for supplying compressed air to the rotor 16, and air discharge line 12*b* for discharging exhaust compressed air from the rotor 16.

The upper and lower ball bearings 14, 15 are angular contact ball bearings. The upper ball bearing 14 has inner ring 14*a* and outer ring 14*b*, and the lower ball bearing 15 has inner ring 15*a* and outer ring 15*b*. The outer rings 14*b*, 15*b* have an angled or sloped outer race. Between the inner ring 14*a* and the outer ring 14*b* are held a plurality of balls 14*c* supported by bearing cage 14*d* at regular circumferential intervals. Similarly, between the inner ring 15*a* and the outer ring 15*b* are held a plurality of balls 15*c* supported by bearing cage 15*d* at regular circumferential intervals.

Figure 2A:
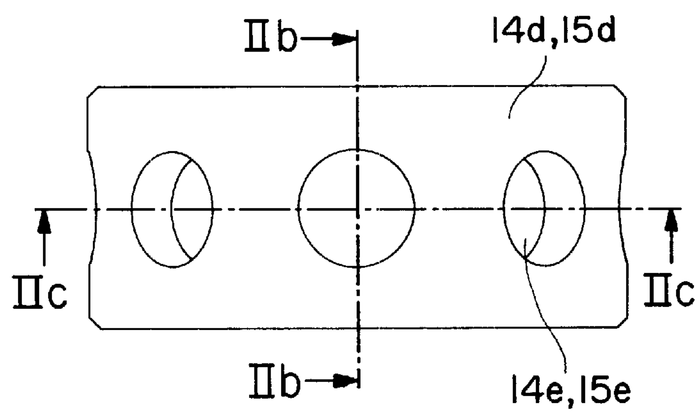
FIG. 2(*a*) is a side view of a bearing cage used in the present invention.
Figure 2B:
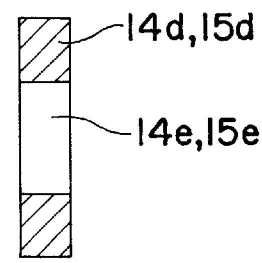
Figure 2C:
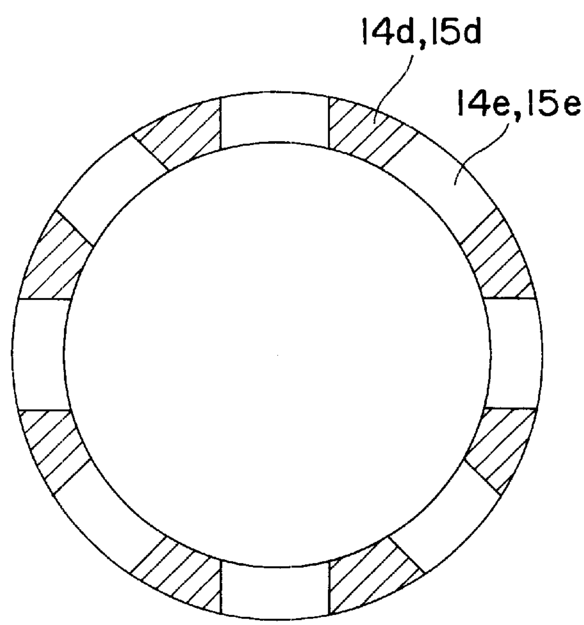
Figure 3:
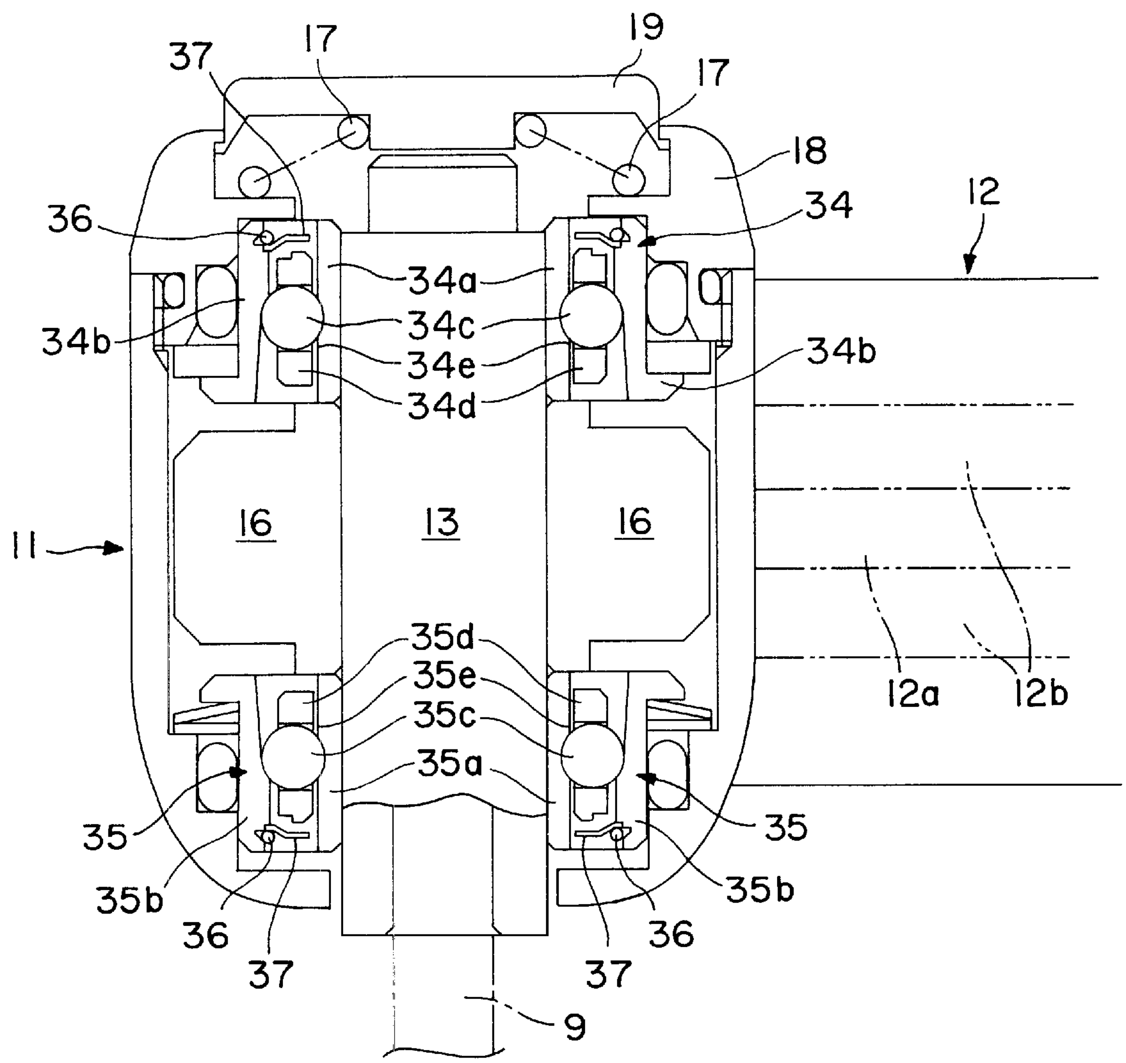
FIG. 3 is a schematic sectional view of a conventional dental handpiece.
Figure 4A:
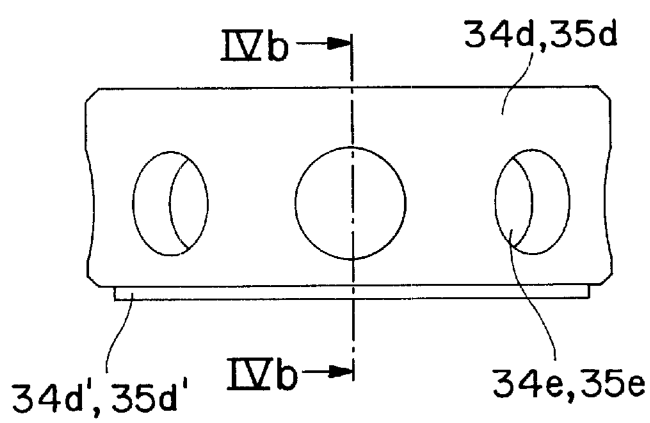
FIG. 4(*a*) is a side view of a conventional bearing cage.
Figure 4B:
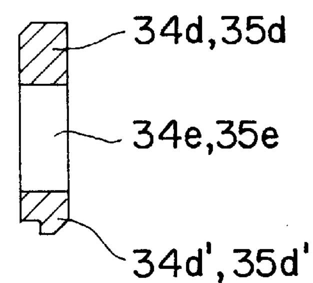

The bearing cages 14*d*, 15*d* are substantially in the form of a ring, and each has a plurality of pockets 14*e*, 15*e*, respectively, for supporting the balls. The pockets 14*e*, 15*e* are arranged circumferentially along the side wall of the cages 14*d*, 15*d*, respectively, at regular intervals and positioned in the middle of the wall in the thrust direction, as shown in FIGS. 2(*a*) to 2(*c*). The bearing cages 14*d*, 15*d* are vertically symmetrical with respect to the pockets 14*e*, 15*e*, respectively.

The bearing cages 14*d*, 15 are preferably made of, for example, a corrosion resistant metal such as stainless steel, or a heat resistant resin such as phenol, polyacetal, or polyamidimide resin, for minimizing degradation through sterilization treatment such as by chemiclaving or autoclaving, to thereby improve durability of the bearings.

The dust controller includes the rotary protruding member 22 and the stationary protruding member 23. The rotary protruding member 22 is generally in the form of an annular ring, and is fixed on the outer surface of the burr sleeve 13 in its lower portion 13*a* by, for example, welding, so that the rotary protruding member 22 rotates integrally with the burr sleeve 13. The rotary protruding member 22 has a thinned facing portion 22*a* extending upwardly in the thrust direction from the upper end of the rotary protruding member 22. This facing portion 22*a* is so positioned as to form a gap between its inner surface and the outer surface of the lower portion 13*a* of the burr sleeve 13.

The stationary protruding member 23 is also generally in the form of an annular ring, and has a radially outer end portion 23*b* bent upwards, which portion 23*b* is fixed to the lower end of the outer ring 15*b* by, for example, by welding. The member 23 also has a radially inner end portion bent downwards in the thrust direction, which portion forms facing portion 23*a* and is located facing to the facing portion 22*a* of the rotary protruding portion 22, defining a gap therebetween.

The outer surface of the lower portion 13*a* of the burr sleeve 13, the facing portion 23*a*, the facing portion 22*a*, and the inner surface of the lower portion of the head housing 11 cooperate to form gaps which establish a labyrinth. One end of the labyrinth communicates with the interior of the lower ball bearing 15, and the other end communicates with outside of the head housing 11. When the burr sleeve 13 is rotated, a high-pressure region is created in the inner most gap having the smallest diameter. This high pressure region effectively blocks off air flow out of the head housing 11, and prevents suction of debris, saliva, blood, and the like through the lower end of the head housing 11 upon stopping of the rotation of the rotor 16, which creates negative pressure in the head housing 11 during rotation.

The facing portion 23*a* of the stationary protruding member 23 and the facing portion 22*a* of the rotary protruding member 22 are located outside of the lower ball bearing 15, and the end portion 23*b* of the stationary protruding member 23 is fixed to the lower end of the outer ring 15*b* of the bearing 15. Thus, the space between the inner ring 15*a* and the outer ring 15*b* is not restricted by the dust controller, and as a result, most of this space may be used for accommodating the bearing cage 15*d* and the balls 15*c*. This enables the vertically symmetrical bearing cage 15*d* having the pockets 15*e* for supporting the balls 15*c* in the middle in the thrust direction, to be positioned between the inner ring 15*a* and the outer ring 15*b*. Due to its vertical symmetry, the bearing cage 15*d* has improved stability, and thus does not contact the balls 15*c*, rattling up and down unstably, resulting in reduction of undesirable shaking of the handpiece and uncomfortable noise. The vertical symmetry of the bearing cage 15*d* also eliminates necessity of special systems and steps for adjusting the vertical orientation of the bearing cage in assembly of the ball bearings 14, 15, reducing the manufacturing cost of the handpiece.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising:

a burr sleeve for detachably holding a dental treatment tool therein;

upper and lower ball bearings for rotatably supporting said burr sleeve, wherein said upper and lower ball bearings are angular contact ball bearings each having a bearing cage, said bearing cage having apertures for supporting balls of said ball bearings therein, said apertures being located substantially in the middle of said bearing cage in a thrust direction;

a rotor fixed to said burr sleeve between said upper and lower ball bearings and rotated by compressed air for rotatably driving said burr sleeve; and a dust controller including a rotary protruding member fixed on an outer surface of said burr sleeve and rotating integrally with said burr sleeve, and a stationary protruding member attached to a stationary part of said handpiece;

wherein said stationary protruding member has a radially inner end portion extended radially inwardly beyond the inner ring of the lower ball bearing, said radially inner end portion having a surface facing to said rotary protruding member to define a gap there between, said gap being located outside of said lower ball bearing; and wherein said burr sleeve has an outer surface substantially flush with an outermost surface of said rotary protruding member.

2. The dental handpiece of claim 1, wherein each of said angular contact ball bearings has an outer ring having an angled outer race.

3. The dental handpiece of claim 1, wherein said stationary protruding member is attached to an outer ring of said lower ball bearing.

4. The dental handpiece of claim 1, wherein said bearing cage is substantially in the form of a ring.

5. The dental handpiece of claim 1, wherein a shield cover is not interposed between inner and outer rings of said upper and lower ball bearings.

6. The dental handpiece of claim 1, wherein said rotary protruding member has a thinned facing portion extending upwardly in said thrust direction from an upper end of the rotary protruding member.

* * * * *